United States Patent
Larsen et al.

(10) Patent No.: US 10,570,078 B2
(45) Date of Patent: Feb. 25, 2020

(54) THERMOLYTIC FRAGMENTATION OF SUGARS

(71) Applicant: HALDOR TOPSØE A/S, Kgs. Lyngby (DK)

(72) Inventors: Morten Boberg Larsen, Smorum (DK); Christian Mårup Osmundsen, Gentofte (DK); Esben Taarning, Frederiksberg (DK)

(73) Assignee: HALDOR TOPSØE A/S, KGS. Lyngby (DK)

( * ) Notice: Subject to any disclaimer, the term of this patent is extended or adjusted under 35 U.S.C. 154(b) by 0 days.

(21) Appl. No.: 16/094,684

(22) PCT Filed: Jun. 15, 2017

(86) PCT No.: PCT/EP2017/064712
§ 371 (c)(1),
(2) Date: Oct. 18, 2018

(87) PCT Pub. No.: WO2017/216311
PCT Pub. Date: Dec. 21, 2017

(65) Prior Publication Data
US 2019/0119187 A1 Apr. 25, 2019

(30) Foreign Application Priority Data
Jun. 16, 2016 (DK) ................... 2016 00351
Jun. 22, 2016 (DK) ................... 2016 00371

(51) Int. Cl.
| | | |
|---|---|---|
| C07C 45/00 | (2006.01) | |
| C07C 27/00 | (2006.01) | |
| B01J 6/00 | (2006.01) | |
| C07C 45/60 | (2006.01) | |
| B01J 8/18 | (2006.01) | |
| B01J 8/00 | (2006.01) | |
| B01J 8/38 | (2006.01) | |
| B01J 8/08 | (2006.01) | |
| B01J 8/26 | (2006.01) | |
| C07C 27/04 | (2006.01) | |
| C07C 31/04 | (2006.01) | |
| C07C 31/08 | (2006.01) | |
| C07C 31/10 | (2006.01) | |
| C07C 47/19 | (2006.01) | |

(52) U.S. Cl.
CPC ............ *C07C 45/60* (2013.01); *B01J 6/008* (2013.01); *B01J 8/003* (2013.01); *B01J 8/0055* (2013.01); *B01J 8/0065* (2013.01); *B01J 8/08* (2013.01); *B01J 8/1818* (2013.01); *B01J 8/1836* (2013.01); *B01J 8/1863* (2013.01); *B01J 8/26* (2013.01); *B01J 8/388* (2013.01); *C07C 27/00* (2013.01); *C07C 27/04* (2013.01); *B01J 2208/0038* (2013.01); *B01J 2208/00362* (2013.01); *B01J 2208/00504* (2013.01); *B01J 2208/00513* (2013.01); *B01J 2208/00902* (2013.01); *B01J 2208/00911* (2013.01); *C07C 31/04* (2013.01); *C07C 31/08* (2013.01); *C07C 31/10* (2013.01); *C07C 47/19* (2013.01)

(58) Field of Classification Search
CPC .......... C07C 45/60; C07C 27/04; B01J 6/008
See application file for complete search history.

(56) References Cited

U.S. PATENT DOCUMENTS

| | | | |
|---|---|---|---|
| 5,302,280 | A | 4/1994 | Lomas et al. |
| 5,393,542 | A | 2/1995 | Stradal et al. |
| 5,397,582 | A | 3/1995 | Underwood et al. |
| 7,094,932 | B2 | 8/2006 | Majerski et al. |
| 2012/0160741 | A1 | 6/2012 | Gong et al. |
| 2015/0329449 | A1 | 11/2015 | Schreck et al. |

FOREIGN PATENT DOCUMENTS

| | | |
|---|---|---|
| WO | 9217076 A1 | 10/1992 |
| WO | 2012115754 A2 | 8/2012 |
| WO | 2014131764 A1 | 9/2014 |
| WO | 2016001136 A1 | 1/2016 |
| WO | 2016001169 A1 | 1/2016 |
| WO | 2017064267 A1 | 4/2017 |

OTHER PUBLICATIONS

International Search Report (PCT/ISA/210) dated Sep. 26, 2017, by the European Patent Office as the International Searching Authority for International Application No. PCT/EP2017/064712.
Search Report dated Nov. 10, 2016, by the Danish Patent Office for Application No. PA 2016 00351.
Search Report dated Nov. 10, 2016, by the Danish Patent Office for Application No. PA 2016 00371.
Written Opinion (PCT/ISA/237) dated Sep. 26, 2017, by the European Patent Office as the International Searching Authority for International Application No. PCT/EP2017/064712.

*Primary Examiner* — Sikarl A Witherspoon
(74) *Attorney, Agent, or Firm* — Buchanan Ingersoll & Rooney P.C.

(57) ABSTRACT

A process for large scale and energy efficient product of oxygenates from sugar is disclosed in which a sugar feedstock is introduced into a thermolytic fragmentation reactor comprising a fluidized stream of heat carrying particles. The heat carrying particles may be separated from the fluidized stream prior to cooling the fragmentation product and may be directed to a reheater to reheat the particles and recirculate the heated particles to the fragmentation reactor.

39 Claims, 4 Drawing Sheets

THERMOLYTIC FRAGMENTATION OF SUGARS

FIELD OF THE INVENTION

The present invention relates to a process for converting a sugar feedstock into a $C_1$-$C_3$ oxygenate product and a system suitable for performing the process. The process and the system are suitable for industrial application, and the process may be performed as a large scale, continuous process.

BACKGROUND

Biomass is of particular interest as a raw material due to its potential for supplementing and possibly replacing petroleum as a feedstock for the preparation of commercial chemicals. In recent years various technologies for exploiting biomass have been investigated. Carbohydrates represent a large fraction of biomass, and various strategies for their efficient use as a feedstock for the preparation of commercial chemicals are being established. These strategies include various fermentation-based processes, pyrolysis, and different processes, such as hydrogenolysis or hydroformylation or acid catalyzed dehydration.

Examples of chemicals produced from biomass include: substitute natural gas, biofuels, such as ethanol and biodiesel, food browning materials, and commercial chemicals, such as diols (ethylene glycol and propylene glycol), acids (lactic acid, acrylic acid, and levulinic acid) and a wide range of other important chemical intermediates (epichlorohydrin, isoprene, furfural, and synthesis gas).

Within the field of pyrolysis, efforts have been focused on using feedstocks based on solid biomass and other cellulosic materials for producing the above chemicals.

Some efforts have been made to use sugars as feedstock for producing food browning materials, which comprise a large amount of glycolaldehyde (also termed hydroxyacetealdehyde) as the key browning agent.

U.S. Pat. No. 5,397,582 and the corresponding WO 92/17076 (Underwood) describes a method for preparation of 'liquid smoke' for browning foodstuffs by injecting sugar and/or starch into two alternative types of gas-solid contact reactors. One reactor hype is a 'downer' type, where the sugar is contacted with the heat carrier (e.g. sand) to produce pyrolysis products, and another is an up-flow type fluidized bed reactor. In the latter reactor the feedstock is injected into heat carrier particles in the form of sand. During the thermolytic fragmentation, a product vapour is formed. The stream of product vapour and spent heat carrier particles is transferred to two consecutive external cyclones and the resulting vapour stream is condensed. The heat carrier particles including char residues are recycled from the first stage cyclone to the bottom of the fragmentation reactor. The residence time of the product vapours is from 0.03 to 2 seconds, the fragmentation temperature is 400-1000° C., and quenching of pyrolysis vapours to less than 300° C. takes place within less than 0.6 s. It is unclear how the heat for reheating spent heat carrier particles is provided. Pyrolyzing powdered starch in this apparatus at 550° C. provides a pyrolysis liquid wherein half of the organics recovered was glycolaldehyde.

U.S. Pat. No. 7,094,932 (Majerski) describes a method of producing a food browning ingredient by thermolytic fragmentation of an aqueous solution of sugar, and in particular glucose, into a pyrolysis product with a high concentration of glycolaldehyde. The method uses a dense fluidized bed of sand particles (also referred to as a bubbling bed). The glucose solution comprising 25-99% of water is introduced into the reactor bed and reacted at a temperature of 500-600° C. The residence time in the reactor is suggested to be 0.1-5 seconds. The heat is provided by electrical heating. The gaseous reaction product is condensed in a surface condenser. The yields of glycolaldehyde in the condensed liquid fragmentation product are on mass basis at least 50% by weight of sugar fed to the reactor. The liquid fragmentation product comprises $C_1$-$C_3$ oxygenate compounds including formaldehyde, glycolaldehyde, glyoxal, pyruvaldehyde and acetol. The main product of this reaction is glycolaldehyde, and carbon recovery in condensate of up to 85-89% of the sugar feed has been achieved. In example 6 of U.S. Pat. No. 7,094,932 the method was scaled up by feeding 7.3 kg/hr of a feed containing 50% dextrose monohydrate (glucose) to a larger apparatus of the same type as above, providing a glycolaldehyde yield of 66%. The residence time in this system was 2-3 seconds and the temperature was in the range of 530-560° C. The heat was still provided by electricity.

WO 2014/131764 describes a method of producing ketene from a sugar solution by subjecting the sugar solution to pyrolysis in the presence of a fluidized bed material with a surface area of up to 600 m2/g and at a temperature of less than 700° C. The fluidized bed material is silica and the residence time is 50-150 ms Both Underwood and Majerski have proposed systems for producing a glycolaldehyde rich product by pyrolysing sugars in a reactor using sand particles as heat carriers and having a short residence time in order to provide high conversion rates of the sugar into glycolaldehyde. However, the systems suggested are not suitable for industrial scale conversion of sugars into glycolaldehyde rich C1-C3 oxygenate mixtures by thermolytic fragmentation.

Fluidized bed reactors are used for processing a variety of feedstocks. They can be operated in a number of different fluidization regimens. The preferred regime is selected depending on the feedstock in question and the desired chemistry to be obtained, which gives rise to a large number of different reactor configurations for fluidized bed reactors.

For conversion of biomass into bio-oil by pyrolysis several reactor configurations have been investigated, such as e.g. dense phase (i.e. bubbling fluidized bed) and dilute phase (i.e. riser) reactors as well as radically different reactor types, such as ablative pyrolysis reactors.

WO 2012/115754 describes a pyrolysis method where solid biomass, such as wood or other plant derived material and a solid heat carrier, such as sand, are mixed at the bottom of a riser reactor and subjected to pyrolysis conditions, to provide a pyrolysis effluent. The pyrolysis effluent is led to a cyclone separator where it is separated into (1) a solids-enriched fraction comprising both solid char and a recycled portion of the solid heat carrier and (2) a solids-depleted fraction comprising pyrolysis products. The pyrolysis products include raw pyrolysis oil and other valuable chemicals, such as carboxylic acids, phenolics, and ketones. The solids-enriched fraction is directed to a reheater reactor comprising a fluidized bed of heat carrier particles wherein the solid char by-product is combusted in the presence of an oxygen containing gas and a quench medium is added in order to reduce the temperature in the reheater reactor. Reheated solid heat carrier is recycled to the pyrolysis riser reactor, where heat carrier particles in turn transfer heat to the pyrolysis reaction mixture to drive the pyrolysis reaction. The vaporous pyrolysis products are cooled and recovered.

Other applications of fluidized beds are for the cracking of hydrocarbons either catalytically of thermally. Catalytic cracking can be performed by the Fluid Catalytic Cracking (FCC) process, where high-boiling petroleum fractions are converted into comparatively lighter products, such as gasoline. Examples of thermal cracking are the Fluid Coking process, where heavy oil fractions, i.e. pitch, is converted into gas oil, or Thermal Cracking processes, where naphtha is converted into ethylene and propylene. These cracking processes are mostly performed in circulating fluidized bed systems One such apparatus suitable for cracking light and heavy FCC feedstocks is described in U.S. Pat. No. 5,302,280 (Lomas). The system described includes a riser reactor for cracking the feedstock using a catalyst. After cracking, the catalyst particles are separated from the vapours and transported to a regenerator reactor, and the vapours are quenched. The catalyst particles are contacted with an oxygen containing stream in a dense fluidized bed resulting in combustion of residual coke to provide heat to the catalyst and to remove the coke from the catalyst particles.

Accordingly, new uses of $C_1$-$C_3$ oxygenate products are being developed and an increasing demand for those products are expected. Such oxygenate products may e.g. be used for producing ethylene glycol and propylene glycol by subjecting the oxygenate product to hydrogenation (see e.g. WO 2016/001169) or for scavenging hydrogen sulphide as described in WO 2017/064267. However, many other uses may be envisaged. To the best of our knowledge, no systems nor processes exist which are in fact suitable for large scale thermolytic conversion of sugars into glycolaldehyde rich mixtures in high yields.

Thus there is still a need for a high yielding and improved process for the preparation of $C_1$-$C_3$ oxygenates from sugars suitable for large scale production, as well as for systems for use in such processes.

SUMMARY OF THE INVENTION

The present inventors, having a desire to produce $C_1$-$C_3$ oxygenates from sustainable sources of high purity and with high yield and efficiency, have found that the processes and systems available for performing thermolytic fragmentation (pyrolysis) of sustainable sources have various drawbacks making them unsuitable for such use in industrial scale.

The inventors have now found a process for producing high purity $C_1$-$C_3$ oxygenates in industrial scale. The process involves carrying out thermolytic fragmentation of a sugar solution in a fragmentation reactor, in which a fluidized bed of heat carrying particles receives the sugar solution and transforms into a riser type reactor, a major fraction of the particles are removed from the product stream followed by a quench of the product stream, and the particles removed are transferred to a reheater reactor for heating and recirculating the heated particles to the fragmentation reactor. Such process, results in a process which is highly energy efficient and yet provides very high yield of $C_1$-$C_3$ oxygenates. The inventors also found, that when sugar is the feedstock, reheating the heat carrying particles required supply of heat from an external source and that it was advantageous to perform the reheating in a separate reactor.

According to an aspect of the present invention a process is provided for thermolytic fragmentation of a sugar into $C_1$-$C_3$ oxygenates, said process comprising the steps of:
a) providing particles carrying heat and suitable for fluidization;
b) providing a fluidized bed fragmentation reactor comprising a riser and suitable for conducting thermolytic fragmentation and suitable tor fluidizing a stream of particles;
c) providing a feedstock solution comprising a sugar;
d) introducing the particles into the fragmentation reactor at a rate sufficient to maintain a temperature of at least 250° C., such as at least 300, 350, 400 or 450° C., after the thermolytic fragmentation has taken place;
e) introducing the feedstock into the fluidized stream of particles to obtain thermolytic fragmentation of the sugar to produce a particle dense fragmentation product; then
f) separating a fraction of the particles from the particle dense fragmentation product to produce a particle lean fragmentation product;
g) quenching the particle lean fragmentation product at least 50° C. such that from introducing the feedstock into the particle containing fluidization stream to the quench is performed the mean residence time of the gas is maximum 5, such as maximum 3 seconds, such as maximum 2, 1, 0.8, or 0.6 seconds; and
h) recovering the crude fragmentation product,
i) transferring the particles separated in step f) to a reheater for heating; and
j) recirculating the heated particles to the fragmentation reactor.

Such a process has the advantages of providing an energy efficient process of producing a crude fragmentation product having a high yield of $C_1$-$C_3$ oxygenates and a low content of unwanted side products. This is obtained through a combination of the features of the invention, which includes using a sugar solution as feedstock, high heat transfer rate, short fragmentation product vapour residence time, first particle removal before quenching the fragmentation product vapour, quenching the fragmentation product vapour rapidly after the first separation, and reheating the particles in an external reheater. The process ensures a high energy efficiency and is suitable for use in large scale production of $C_1$-$C_3$ oxygenates, e.g. for further processing to ethylene glycol and propylene glycol. The process is suitable for a continuous production of $C_1$-$C_3$ oxygenates.

The heat carrying particles are heated in a heater outside the fragmentation reactor and subsequently introduced into the fragmentation reactor, for example by direct contact with a hot gas in another reactor. The particles are heated to a temperature sufficient to carry heat from the particle heater into the fragmentation reactor to accommodate a transfer of heat to the sugar solution sufficient for the thermolytic fragmentation of the sugar to take place and for obtaining a fragmentation product stream which comprises a large fraction of $C_1$-$C_3$ oxygenates. The flow of particles within the fluidized bed may be adjusted to the feedstock flow so as to provide the desired amount of heat to the feedstock. Particles of materials with a high heat capacity require a lower mass flow rate than particles of materials with a lower heat capacity. In an embodiment according to the present invention, the particles of step a) are introduced into the fragmentation reactor at a mass flow rate of at least 10 kg/s, preferably at a mass flow rate of 10-1000 kg/s.

In the present context, the fragmentation product is meant to refer to the vaporous stream resulting from the thermolytic fragmentation of sugar. The particle dense fragmentation product is meant to refer to the fragmentation product before first particle separation and comprising a higher load of particles and the particle lean fragmentation product is meant to refer to the fragmentation product after first particle separation and comprising less particles. The crude fragmentation product is meant to refer to the stream recovered from the fragmentation reactor where a fraction of the particles has been removed.

The particles are preferably selected from the group consisting of sand, silica, glass, alumina, steel, and silicon carbide.

Preferably, the mean particle size of the particles is from 20-400 μm, such as from 20-300, 20-200 or 20-100 μm.

A fluidized bed reactor is a reactor which accommodates a bed of particles to be fluidized by a fluidization gas stream which is usually introduced at the bottom of the reactor. The velocity and physical properties of the fluidization gas stream combined with the physical properties of the particles regulates the fluidization state of the particles within the bed. A dense bed/turbulent bed/bubbling bed is usually considered having a superficial velocity of the fluidization gas stream within the reactor of 0.1-2 m/s. A fast bed (or a riser/transport reactor) is usually considered to have a superficial velocity of fluidization stream within the reactor of 3-22 m/s. The exact velocity range is however dependent on the physical properties of the particles and fluidization gas and can be determined experimentally or calculated by a person skilled in the art.

In the present invention the thermolytic fragmentation is performed in a fluidized bed reactor operating in the fast fluidization regime, i.e. a riser type reactor. In general, the riser is a vertically extending reactor, which in the lower part comprises a fluidization stream inlet, a particle inlet and a feedstock inlet, and wherein the particle inlet is provided downstream the fluidization inlet, and the feedstock inlet is provided downstream the particle inlet. For the purpose of the present invention, the particles may form a dense phase fluidized bed in the zone between the particle inlet and the feedstock inlet. The fluidization stream and thus the fluidization stream inlet could be dispensed with. For example the feedstock could be introduced right after the heat carrying particles and thus serve as fluidization stream.

The temperature of the particles at the particle inlet of the fragmentation reactor is preferably at least 300° C., such as at least 400, 450, 500, 550, 600 or 650° C.

Preferably, the temperature of the particles at the particle inlet is within the range of from 300-800° C., such as in the range of from 400-800 or 450-650° C.

The feedstock may be introduced at any point after introducing the heat carrying particles. When the feedstock meets the heat carrying particles, a vaporisation zone is formed in which the solvent evaporates and gaseous products starts to be generated from the sugar fragmentation. This results in an increase in toe superficial velocity of the gas thereby entraining the heat carrying particles. Accordingly, downstream the feedstock inlet, the heat carrying particles and the feedstock form a fast bed above the vaporisation zone, which may be referred to as a riser. According to an embodiment of the present invention, the feedstock inlet is provided in the lower part of the riser.

In an embodiment according to the present invention, the fragmentation reactor comprises a first particle separator downstream the riser to separate a fraction of the particles from the particle dense fragmentation product. The first particle separator may be referred to as a riser termination in cases where it is placed immediately after the riser. When a first particle separator is included prior to cooling or quenching the fragmentation product stream, the advantage is that a cooling of the fraction of the heat carrying particles may be avoided during the cooling of the fragmentation product stream with the result that an unnecessary heat loss is avoided in the process.

In an embodiment of the present invention, a major fraction of the heat carrying particles are separated in the first particle separator. Accordingly, more than 50% by weight, such as at least 60, 70, 80,90, 95 or even 99% by weight, of the heat carrying particles are separated from the particle dense fragmentation product by the first particle separator. The first particle separator is preferably a change of direction separator. This type of separator quickly separates the fragmentation product from the particles, allowing the quench to be performed more rapidly and thus minimizing the fragmentation products exposure to heat and thereby reducing the degree of degradation and further reaction of the oxygenate mixture within the fragmentation product. The rapid heating of the feedstock and the rapid cooling of the fragmentation product thus achieved are highly advantageous, since the average period of time that the oxygenates within the fragmentation product are exposed to heat and thus to a heat degradation is very short, yet the major part of the sugar introduced into the reactor is exposed to sufficient heat for the thermolytic fragmentation to proceed.

Accordingly, the mean residence time of the gas from the feedstock inlet to the quenching is within the range of from 0.01 to 5 seconds, such as from 0.01 to 3, 0.1 to 1 or from 0.3 to 0.8 seconds. The mean residence time within the riser required for the major part of the sugar introduced into the reactor to be exposed to sufficient heat for the thermolytic fragmentation to proceed depends on the rate of the heat transfer from the particles. This rate of heat transfer depends on factors such as particle temperature at the inlet, heat capacity of the particles, solvent of the sugar solution etc. The velocity of the particles and the reactor design may be adapted to supply sufficient yet not excessive heat to for the thermolytic fragmentation. The heating rate of feedstock that can be achieved with this apparatus is very high and is above 1000° C. per second. An advantage of separating the heat carrying particles from the particle dense fragmentation product prior to quenching is that the remaining heat of the heat carrying particles may be recovered.

In an embodiment according to the present invention, product gas from the fragmentation reactor is stripped from the particles before they are being transferred to the reheater. This could further enhance the product yield.

In an embodiment according to the present invention, the reactor composes a quench downstream the first particle separator. An advantage of carrying out a quenching after separation of a fraction of the heat carrying particles is that less energy is lost. This improves the energy efficiency of the process. In addition, the quenching of the fragmentation product stream proceeds faster and requires transfer of less energy when less heat carrying particles are present. Preferably, the quenching is performed by introducing a liquid, such as water or recycled streams from downstream processes of the fragmentation reactor, into the particle lean fragmentation product. The liquid may be an intermediate or end product recovered downstream of the thermolytic fragmentation. This improves toe energy efficiency further. Alternatively, the quenching may be performed by an indirect heat exchange or by admitting colder particles into the particle lean fragmentation product. Preferably, the particles are the same type of particles as the particles used as heat carrying particles, only cooler. An advantage of this is that the particles may enter into and form part of the recirculation stream of particles. The liquid may be injected or sprayed into the particle lean fragmentation product, such as through nozzles within the fragmentation reactor.

In an embodiment according to the present invention, the particle lean fragmentation product is quenched to a temperature below 450° C., such as below 400, 350 or 300° C.

The thermolytic fragmentation of sugar is an endothermic reaction, mainly due to evaporation of feedstock. Therefore, the heat carrying particles will lose some heat during the process if no additional heat is provided. According to an embodiment of the present invention, the temperature difference of the particles between the particle inlet and the particle outlet of the fragmentation reactor is within the range of from 10-600° C., such as from 50-250° C. According to another embodiment of the present invention, the temperature of the heat carrying particles at the particle outlet of the fragmentation reactor is in the range of from 250-700, such as from 300-600 or 350-550° C.

The heat carrying particles separated in the first particle separator from the particle dense fragmentation product is transferred to a reheater in which the heat carrying particles are heated and subsequently recirculated to the fragmentation reactor. Such external heating of the heat carrying particles has the advantage that the source of heat does not affect the thermolytic fragmentation reaction. It thus allows a heating process which involves combustion in the presence of excess oxygen to provide heat for driving the endothermic reaction without the oxygen affecting an over-oxidation of the sugar.

In an embodiment according to the present invention, the reheater comprises a heating chamber for heating the heat carrying particles and a source for heating. According to an embodiment of the present invention, the reheater is a fluidized bed reactor comprising a riser.

Preferably the heat carrying particles have a reheater exit temperature in the range of from 300-800° C., such as from 400-800, 400-700 or 500-700° C.

The fragmentation reactor may comprise a second particle separator downstream the quench. This is to remove any remaining heat carrying particles in order to obtain a more pure fragmentation product. Removing as many particles as possible reduces the wear and disturbance of downstream processes. In the present context "remove" is intended to mean "reduce the amount of". In addition, the separated heat carrying particles may be transferred to the reheater.

Alternatively, the heat carrying particles removed in the second particle separator, which have been exposed to cooling, may be further cooled and used as quench particles in the fragmentation reactor.

An advantage of using the heat carrying particles for providing heat to the thermolytic fragmentation is that there is no need for the fragmentation reactor to comprise means for heating neither internally nor on the surface of the reactor. However, this does not mean that the fragmentation reactor cannot comprise such heating arrangements. The use of particles to provide the heat for the thermolytic fragmentation of sugar is advantageous for several reasons. For instance, the particles have a large surface area for accommodating a heat transfer to large amounts of sugar. Even if the process is scaled up these advantages still apply. In fact, a sufficient heat transfer is unlikely to limit the productivity of the process according to the invention.

The feedstock solution of step c) comprises a sugar. In an embodiment of the present invention, the feedstock solution is an aqueous solution of a sugar. In the present context "a sugar" is intended to refer to a carbohydrate comprising one or more C6 and/or C5 saccharide units, mainly in the form of mono- and/or di-saccharide(s). In an embodiment according to the present invention, the sugar is selected from the group consisting of sucrose, lactose, xylose, arabinose, ribose, mannose, tagatose, galactose, glucose and fructose; or mixtures thereof. The sugar may also be in the form of a sugar syrup. Thermolytic fragmentation of glucose provides a high yield of glycolaldehyde. Accordingly, sugars comprising glucose units are preferred when it is desired to produce glycolaldehyde in high yields.

According to a further embodiment of the present invention, the feedstock solution is introduced into the fluidized bed reaction chamber in the form of an aqueous solution comprising up to 90% by weigh of the sugar. According to yet another embodiment, the feedstock solution is introduced into the fluidized bed reaction chamber in form of an aqueous solution comprising from 10% to 90% by weight of the sugar, such as from 30% to 80%, or 40% to 70% by weight of the sugar.

The $C_1$-$C_3$ oxygenates produced in the process according to the invention consist primarily of formaldehyde (C1), glycolaldehyde (C2), glyoxal (C2), pyruvaldehyde (C3) and acetol (C3). However, for most uses, the C2- and the C3 oxygenates are the most valuable products. The crude fragmentation product recovered from the process according to the present invention comprises a mixture of those $C_1$-$C_3$ oxygenates. This may interchangeably be referred to as a $C_1$-$C_3$ oxygenate mixture, a $C_1$-$C_3$ oxygenate product, and $C_1$-$C_3$ oxygenates. In an embodiment of the present invention, the fragmentation product is rich in glycolaldehyde, meaning that at least 50%, such as at least 60% or 70% by weight of the $C_1$-$C_3$ oxygenate mixture is glycolaldehyde. In another embodiment of the present invention, at least 50%, such as at least 60%, 70% or 80% by weight of the $C_1$-$C_3$ oxygenate mixture is glycolaldehyde or glyoxal. In yet another embodiment of the present invention, at least 3%, such as at least 5% or 7% by weigh of the $C_1$-$C_3$ oxygenate mixture is pyruvaldehyde. In yet another embodiment of the present invention, at least 3%, such as at least 5% or 7% by weight of the $C_1$-$C_3$ oxygenate mixture is pyruvaldehyde or acetol.

The process according to the present invention is suitable for large scale production of $C_1$-$C_3$ oxygenates. Accordingly, it is suitable for processing amounts of sugar of more than 1,000 tons per year per reactor, such as more than 5,000, 10,000, 50,000, 100,000 or 1000,000 tons per year per fragmentation reactor, based on weight of dry sugar.

The process and apparatus according to the present invention have the advantage of ensuring a combined carbon yield of $C_1$-$C_3$ oxygenates above 60 mole %, such as above 70, 75 or 80 mole %. Since $C_2$ and $C_3$ oxygenates are in general more valuable than $C_1$ oxygenates, it is desirable to obtain high yields of $C_2$-$C_3$ oxygenates. According to an embodiment of the present invention the combined carbon yield of $C_2$-$C_3$ oxygenates is above 60 mole %, such as above 70, 75 or 80 mole %. According to another embodiment of the present invention the combined carbon yield of $C_2$ oxygenates is above 50 mole %, such as above 60, 70, 75 or 80 mole %. According to yet another embodiment of the present invention the carbon yield of glycolaldehyde is above 50 mole %, such as above 60, 70, 75 or 80 mole %.

According to an aspect of the present invention the reheater is a riser type reactor (also referred to as a "riser"). An advantage of using this type of reheater is that large amounts of particles may be reheated quickly and that it is possible to separate the combustion reaction from the heating of the heat carrying particles. The heat carrying particles are introduced through a particle inlet and are heated within the reheater riser. The heated particles exit the reheater riser through a reheater particle outlet. Preferably, the particles have a reheater exit temperature in the range of from 400-800° C., such as from 500-700° C. The heated, heat carrying particles are circulated from the reheater particle outlet to the fragmentation reactor particle inlet. The heat carrying particles are transferred from the particle outlet of the fragmentation reactor to the particle inlet of the reheater through a conduit. In an embodiment of the present invention, the particle outlet of the fragmentation reactor is higher than the particle inlet of the reheater to allow gravity to aid in transporting the particles. Similarly, the heated particles are transferred from the particle outlet of the reheater to the particle inlet of the fragmentation reactor through a conduit. In an embodiment of the present invention, the particle outlet of the reheater is higher than the particle inlet of the fragmentation reactor to allow gravity to aid in transporting the particles. An advantage of using riser reactors in both the fragmentation reactor and the reheater is that a circulating fluidized bed system may be used, where the particles are lifted within the risers and gravity then aids in circulating the particles between the two riser systems. This is a great advantage, when producing C1-C3 oxygenate mixtures from sugars in an industrial scale.

In order to obtain high carbon yields, it is desirable that the process produces as little char or coke as possible. However, having low levels of char and coke, results in limited heat generation from combustion of such side products. In the process according to the present invention, low production of char and coke is obtained. This requires a supply of heat from an external source. According to an embodiment of the present invention, the reheater comprises a fuel and combustion air inlet, a burner, a reheater particle inlet, a reheater riser, a reheater particle separator, a reheater gas outlet and a reheater particle outlet. The combustion air may e.g. be atmospheric air or another oxygen containing gas.

The heat may be supplied by means of a burner arranged within the reheater and combusting a fuel in the presence of combustion air. The combustion gas of the burner may be led to the bottom of the reheater riser to mix with the heat carrying particles to form a fluidization stream within the reheater riser.

According to an embodiment of the present invention, combustion of air and fuel is undertaken in a separate burner chamber. The hot combustion gas can then be contacted with particles within the reheater riser, whereby the particles take up heat from the combustion gas. Having a separate burner chamber apart from the reheater particle inlet has the advantage that higher thermal efficiency and low emissions of unburned hydrocarbons can be achieved.

Fuel and air staging burners are known techniques for reduction of NOx emissions for a person skilled in the art. Such burners are also suitable for practicing the present invention. Other methods to reduce the NOx emissions are e.g. recirculating a part of the flue gas of a reheater gas outlet into the burner region so as to lower the oxygen content in the flame zone, or staging of fuel and particles into the reheater riser so as to create zones where the temperatures and oxygen content are lower and hence reduce the NOx formation.

Suitable fuels are e.g. natural gas, oil, coal, pyrolysis gas, gasification gas, hydrogen and carbon monoxide containing gasses, waste products and biomass. Gaseous fuels have an advantage of having no content of ash and hence no risk of ash related problems, such as bed agglomeration, often seen in fluidized beds using for instance solid biomass fuel. In an embodiment of the present invention natural gas is a preferred fuel. It is readily available and the combustion is environmentally friendly compared to other fuels. The combustion temperature is quite high. Therefore it may be preferable to conduct the combustion in a combustion chamber separate from the reheater riser and adapt the feed of the combustion gas to the reheater riser to attain the desired exit temperature of the heated particles.

In an embodiment according to the present invention, excess oxygen from the reheater is stripped from the particles before they are transferred to the fragmentation reactor. This could further enhance the product yield and product purity by minimizing side reactions of oxygenates with O2 in the fragmentation reactor. The stripping chamber is preferably arranged downstream the reheater particle separator and upstream the fragmentation reactor particle inlet.

According to an embodiment of the present invention, the thermolytic fragmentation process is operated as a continuous process. This is an advantage for industrial application.

According to yet another embodiment of the present invention, the thermolytic fragmentation process is carried out in an inert atmosphere, e.g. an atmosphere of nitrogen or steam.

According to an aspect of the invention, a process is provided for the preparation of a $C_1$-$C_3$ hydroxy compound from a sugar, the process comprising the steps of carrying out a thermolytic fragmentation process according to the invention to form a crude fragmentation product comprising $C_1$-$C_3$ oxygenates;

and then subjecting the crude fragmentation product to a hydrogenation to obtain the corresponding $C_1$-$C_3$ hydroxy compounds $C_1$-$C_3$ hydroxy compounds are e.g. ethylene glycol, propylene glycol and methanol.

The process according to the present invention may be carried out in a fragmentation reactor accommodating the use of heat carrying particles in a fluidized bed and accommodating efficient particle separation after the thermolytic fragmentation and efficient reheating of the heat carrying particles.

Accordingly, a system is provided according to the present invention for fragmentation of a sugar composition into $C_1$-$C_3$ oxygenates, which system comprises a fragmentation reactor, said reactor comprising within the reactor, a riser
a first particle separator
a fluidization stream inlet
a particle inlet
a feedstock inlet
a particle outlet
a product outlet,
wherein the riser is arranged within and in the lower part of the fragmentation reactor;
the fluidization stream inlet and the particle inlet are arranged in the lower part of the riser;
the feedstock inlet is arranged in the lower part of the riser above the particle inlet;
the riser is adapted to fluidize particles in the riser;
the first particle separator is arranged in the upper part of the riser and is adapted to separate at least a fraction of the particles from a fluidization stream, and
wherein the reactor further comprises a cooling section arranged downstream the first particle separator in relation to the gas stream, said cooling section being adapted to cool the fluidization stream exiting the first particle separator and the system further comprises a reheater for reheating particles exiting the fragmentation reactor, the reheater comprises a fuel and combustion air inlet, a burner, a reheater particle inlet, a reheater riser, a reheater particle separator, a reheater gas outlet and a reheater particle outlet.

Such an apparatus has the advantage of accommodating a process according to the invention providing an energy efficient process of producing a crude fragmentation product having a high yield of $C_1$-$C_3$ oxygenates and a high recovery rate of carbon in the fragmentation product, said apparatus thus providing a process suitable for a large scale production of e.g. ethylene glycol and propylene glycol from sugars. The apparatus is suitable for a continuous production of $C_1$-$C_3$ oxygenates.

According to an embodiment of the present invention, the system may further comprise a second particle separator within the reactor, said second particle separator being arranged in the upper part of the fragmentation reactor and adapted to separate a further fraction of the particles from the fluidization stream.

According to an embodiment of the present invention, the cooling section is adapted to quench by injecting a liquid into the fragmentation reactor.

According to an embodiment of the present invention, the cooling section is adapted to quench by admitting a colder particle stream into the fragmentation reactor.

According to an embodiment of the present invention, the cooling section comprises an indirect heat exchanger.

According an embodiment of the present invention, the first particle separator is a low volume separator.

According to an embodiment of the present invention, toe first particle separator comprises at least one change of direction separator.

According to an embodiment of the present invention, the first particle separator comprises at least one tube arranged with a first end at the upper part of and in fluid connection with the riser, and where the second end of the tube is pointing downwards and is in fluid connection with and within toe fragmentation reactor and outside the riser.

According to an embodiment of the present invention, the second particle separator is at least one cyclone.

According to an embodiment of the present invention, the burner and the fuel and combustion air inlet is arranged upstream the reheater riser; the reheater particle inlet is arranged in the lower part of said reheater riser downstream the burner; the reheater particle inlet is in fluid connection with the fragmentation reactor particle outlet; and the reheater riser is adapted to reheat the particles exiting the fragmentation reactor by means of gas heated in the burner.

According to an embodiment of the present invention, the reheater particle separator is arranged downstream the reheater riser, and the reheater particle outlet is in fluid connection with the fragmentation reactor particle inlet.

According to an embodiment of the present invention, the burner is arranged in a burner chamber. It may be separated from the riser by a constriction. For example, the cross sectional surface area of the constriction is at least 25% smaller than the cross sectional area of the riser above and that the length of the constricted section is at least 0.5 meters.

BRIEF DESCRIPTION OF THE DRAWINGS

Embodiments of the present invention are explained, by way of examples and with reference to the accompanying drawings. It is to be noted that the appended drawings illustrate only examples of embodiments of this invention, and they are therefore not to be considered limiting of its scope, as the invention may admit to other alternative embodiments.

POSITION NUMBERS

1. Fragmentation reactor
2. Fragmentation riser
3. First particle separator
4. Second particle separator
5. Cooling section
6. Fluidization inlet
7. Particle inlet
8. Feedstock inlet
9. Product outlet
10. Particle outlet
11. Reheater
12. Fuel and combustion air inlet
13. Burner chamber
14. Reheater particle inlet
15. Reheater riser
16. Reheater particle separator
17. Reheater particle outlet
18. Reheater gas outlet
19. Second reheater particle separator
20. Stripper
21. Reheater fluidization gas inlet
22. Secondary reheater fluidization and stripping gas inlet

DETAILED DESCRIPTION

Figure 1:
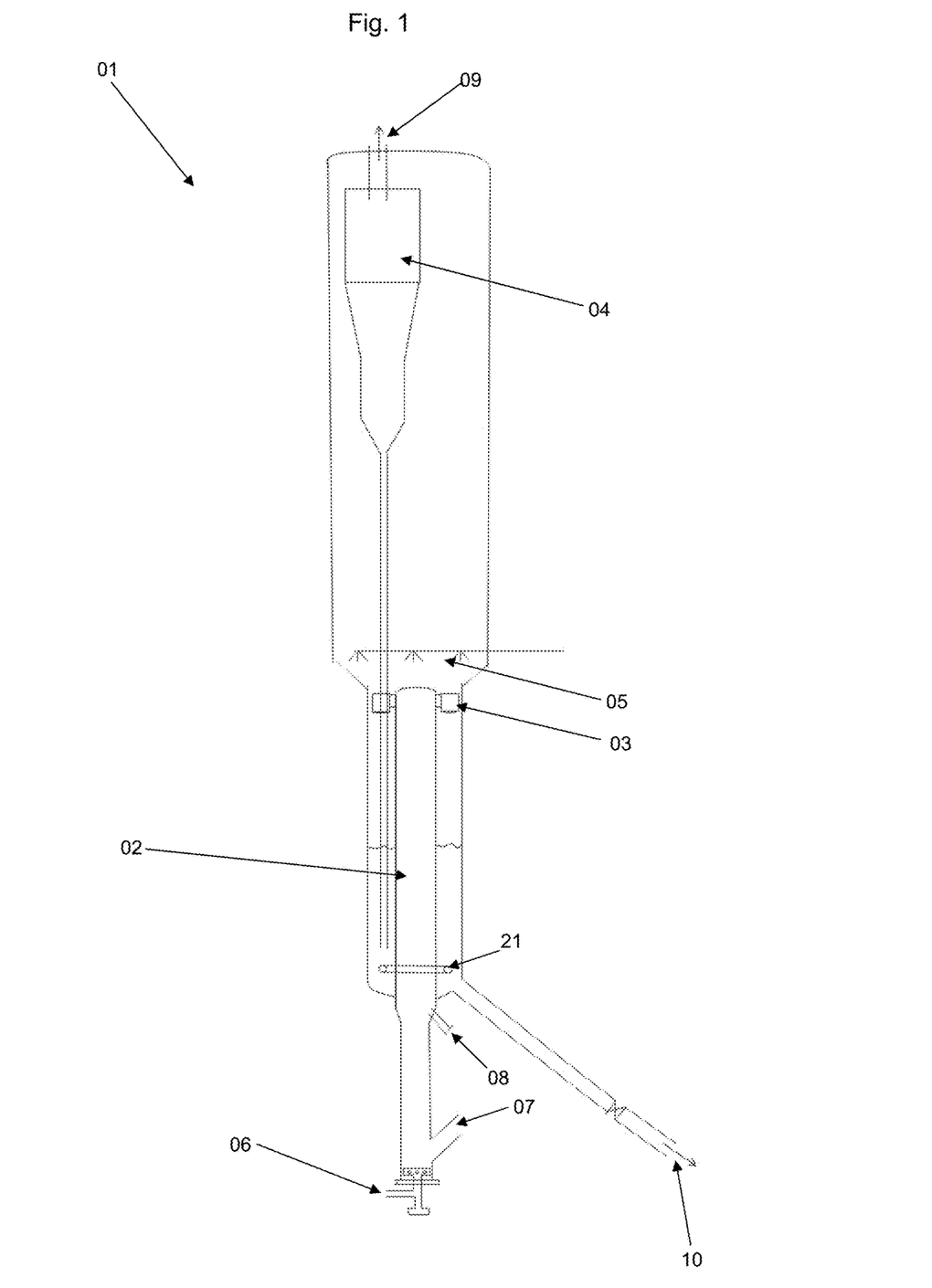
FIG. 1 shows a cross sectional side view of a fragmentation reactor according to an embodiment of the invention.
Figure 4:
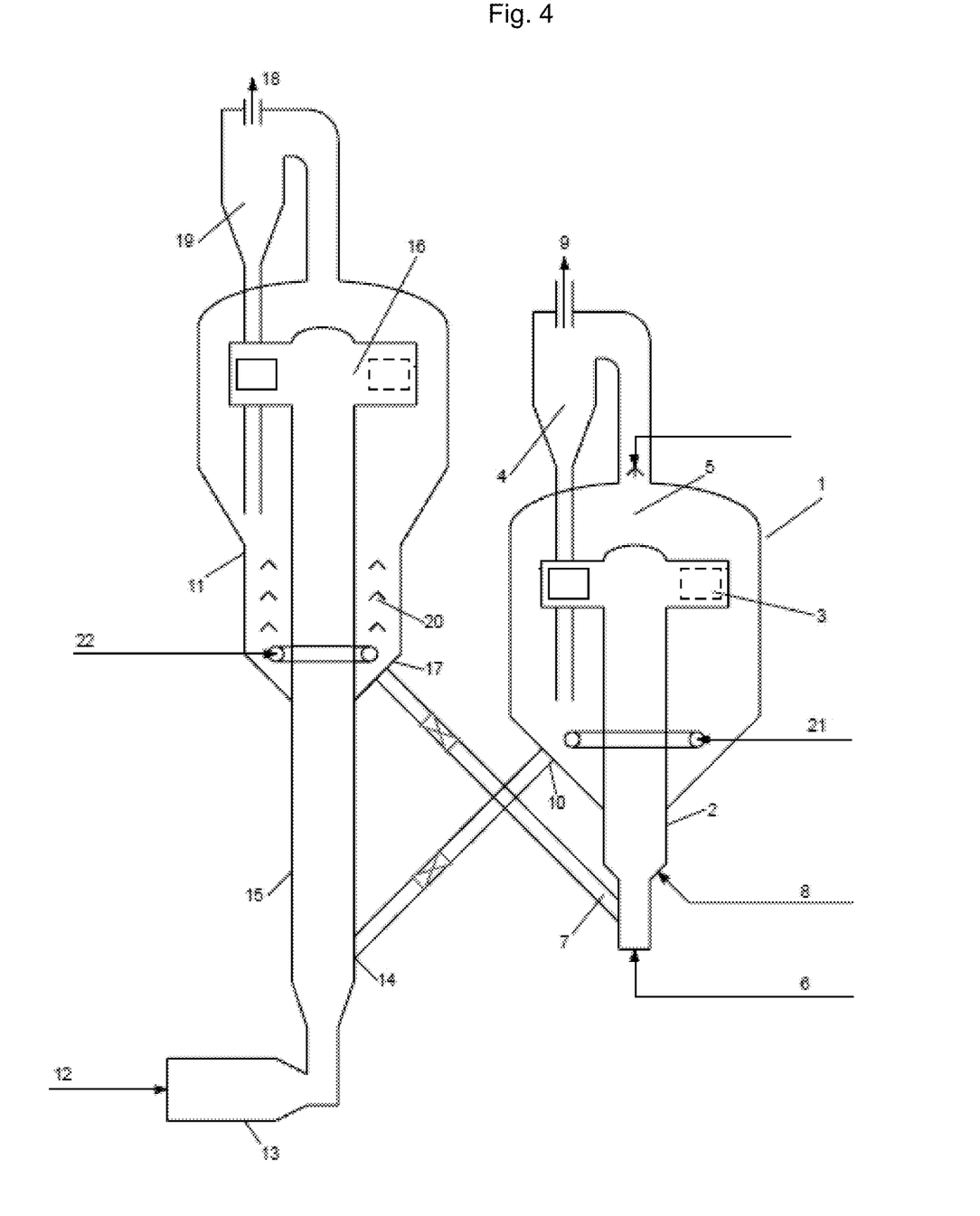
FIG. 4 shows a cross sectional side view of a system comprising a fragmentation reactor in fluid communication with a reheater according to an embodiment of the invention.

As illustrated in FIG. 1 and FIG. 4, the fragmentation reactor of the invention is oblong in the vertical direction. Within the fragmentation reactor a riser 02 is provided, which is oblong with a small cross sectional area relative to the height. This facilitates the possibility of a low residence time of the particles inside the riser. In the lower section of the riser, a fluidization gas inlet 06 is provided which is adapted to provide a fluidization media to the riser and a particle inlet 07. The fluidization media helps to facilitate the movement of the particles from the particle inlet to the feedstock inlet towards the top of the riser. In addition, the fluidization stream can be used to pre-condition the particles before the particles are contacted with the feedstock. Above the particle and fluidization inlet, a feedstock inlet 08 enables the supply of feedstock to the riser. In the embodiment shown, the feedstock inlet is arranged in the lower section of the riser, but the position may vary according to the process demands.

Figure 2:
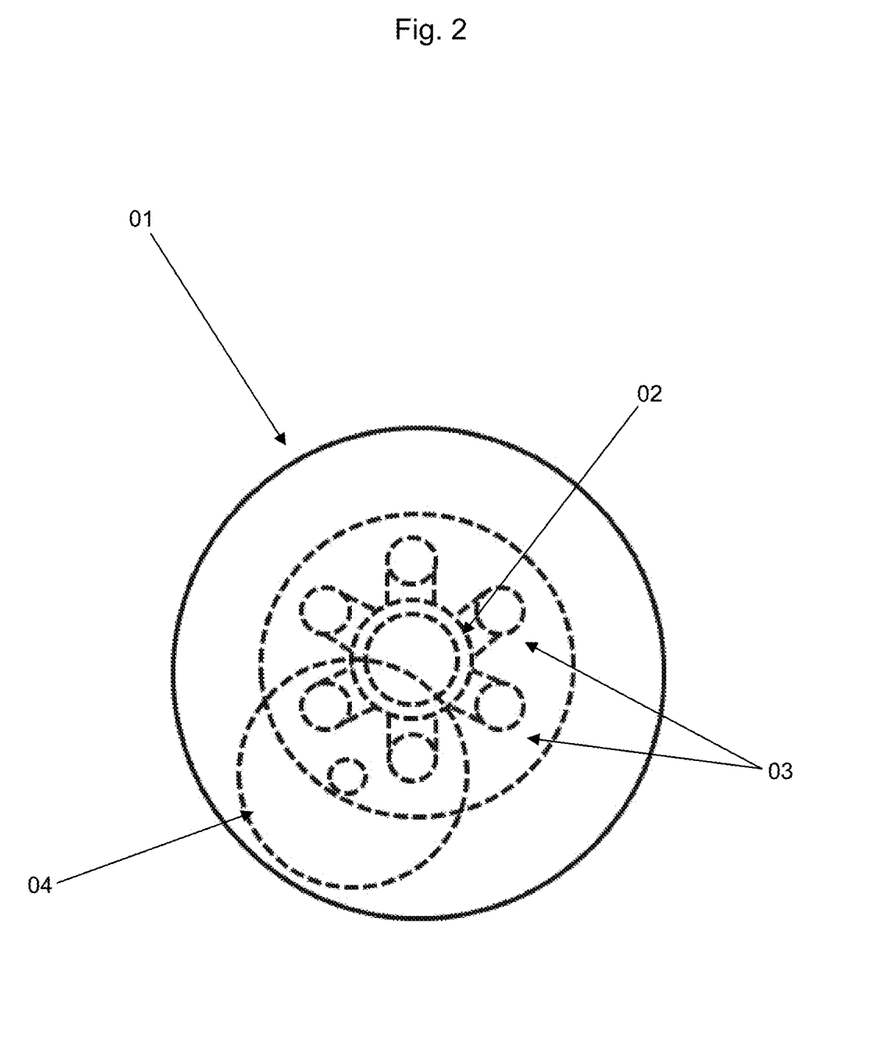
FIG. 2 shows a top view of the fragmentation reactor of the embodiment shown in FIG. 1.
Figure 3:
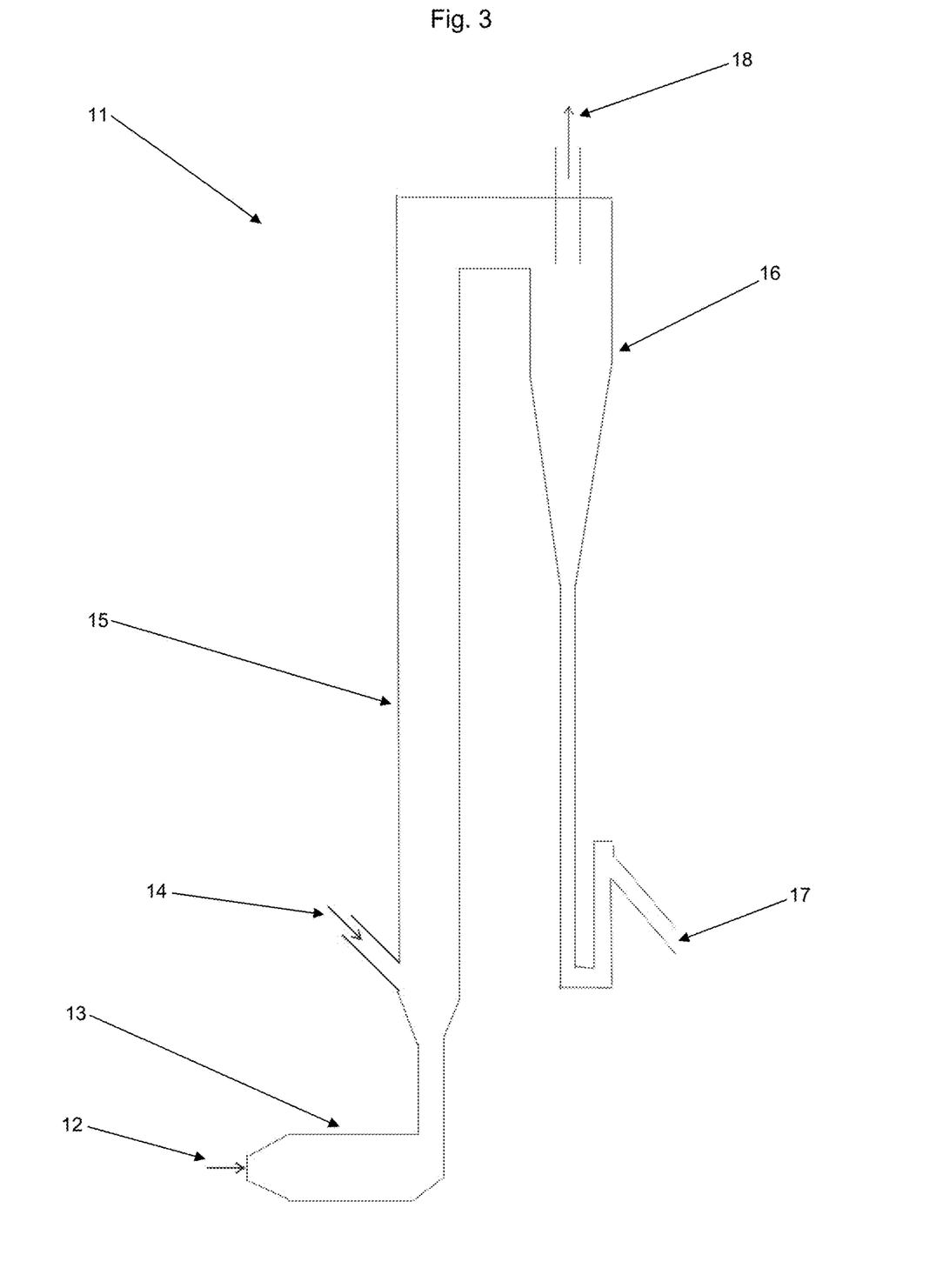
FIG. 3 shows a cross sectional side view of a reheater according to an embodiment of the invention.

When feedstock and particles have interacted in the riser, they are separated when exiting the riser in the first particle separator 03. According to an embodiment of the invention, the first particle separator is adapted to provide a fast separation of particles from the fragmentation product as such a fast separation is highly advantageous to the process. Hence, the particle separator can be of a low residence time type. In the embodiment of FIG. 2 and FIG. 3, the first particle separator comprises exit pipes which change the upwards direction of the exit flow from the riser app. by 180° into a downwards flow direction within the fragmentation reactor and outside the riser, which in the present context is referred to as a change of direction particle separator. In the embodiment of FIG. 4., the first particle separator comprises a gas particle separation forcing a tangential, relatively to the wall of item 1, exit of the riser gas and solid into the vessel of 1 and thereby performing the separation. A part of the particles settles at the bottom part of the fragmentation reactor after exiting the first particle separator. Accordingly, the described features of the riser, the position of feedstock inlet and the low residence time first particle separator provide the possibility of a very low contact time between particles and feedstock depending, of course, also on process parameters such as volume flows and specific dimensions, which all need to be adapted to the process demands.

A cooling section 05 is arranged within the fragmentation reactor above and adjacent the first particle separator. In the present embodiment, the cooling section comprises a quench, where a cooling media such as water or a recycled stream is injected, which rapidly and effectively cools the product by evaporation of the cooling media. Other embodiments such as quenching by introducing a particle stream or indirect heat exchangers may also be employed in the cooling section, whereby the total energy consumption of the fragmentation reactor system may be decreased. The rapid cooling of the product may be essential for the process, to keep a high yield, since the product may be sensitive to prolonged exposure to elevated temperatures.

After cooling the product, it is extracted from the fragmentation reactor via the product outlet 09. In the embodiment shown in FIG. 1 and FIG. 4, an optional further second particle separator 04 is provided in the fragmentation reactor to separate a further fraction of the particles from the product stream before it is extracted. In this section of the fragmentation reactor, the product is already cooled, and thus the residence time is less crucial. A second particle separator, such as for instance a cyclone, is provided, said second particle separator presenting a higher separation efficiency than the change of direction separator alone (item 03). The gas outlet of the cyclone is connected to the product outlet, whereas the particles from the particle outlet of the cyclone are carried to the bottom of the fragmentation reactor (01), where they are maintained fluidized by use of fluidization gas inlet (21). The distribution of fluidization gas over the cross section is ensured using e.g spargers. At the bottom of the fragmentation reactor, a particle outlet 10 enables the spent particles of the fragmentation reactor to be extracted and carried to e.g. reheating in another reactor.

FIG. 2 is a top view of the fragmentation reactor of the embodiment of FIG. 1 as described in the embodiment above. As illustrated, the riser is located in the horizontal cross sectional center of the fragmentation reactor. Furthermore, the plurality of exit pipes forming the first particle separator is shown, as well as the second particle separator which is located off center to the fragmentation reactor.

In FIG. 1 and FIG. 2, the secondary particle separator is placed inside the fragmentation reactor. The secondary particle separator may comprise one or several cyclones. In other embodiments, not shown these cyclones can also be placed outside the fragmentation reactor, e.g. above with diplegs extending through the fragmentation reactor roof or at the side of the fragmentation reactor with inclined diplegs or using e.g. a loop seal or L-valve. By placing the secondary cyclones outside the reactor vessel, the residence time of the oxygenate product in the fragmentation reactor may be decreased. The embodiment of FIG. 4 comprises external cyclones on the fragmentation reactor In FIG. 3 and FIG. 4, a reheater 11 for reheating the particles exiting the fragmentation reactor is shown. The reheater particle inlet 14 is in fluid connection with the fragmentation reactor particle outlet 10, and the reheater particle outlet 17 is in fluid connection with the fragmentation reactor particle inlet 7. The reheater also comprises a riser type fluidized bed, a reheater riser 15, with a burner chamber 13 arranged in fluid connection to the lower part of the riser. A fuel and combustion air inlet 12 enables fuel and combustion air to be provided to the burner, which, when in operation provides heat to the reheater riser. The reheater particle inlet is arranged in the lower part of the reheater riser and enables the particles exiting the fragmentation reactor to enter the reheater riser where they are fluidized in an upwards flow by the hot gas provided by the burner while being heated. The connection between the burner and the reheater particle inlet is deliberately designed to reduce/prevent fall through of particles from the riser and into the combustion chamber. This design could take many different embodiments. In FIG. 3 and FIG. 4, this is illustrated by the constriction between 13 and 15 leading to an increased gas velocity preventing/reducing a fall through of particles. After reheating, the particles are separated from the combustion gas and are led back to the fragmentation reactor. In the embodiment of FIG. 3, the reheater particle separator 16 is a cyclone which enables gas to exit the reheater via the reheater gas outlet 18 while the separated particles exits the reheater via the reheater particle outlet connected to the particle outlet of the cyclone of the reheater. It is to be understood that the extent of separation in the particle separators depends on various process parameters, such as pressure loss in the separator, flow velocities, particle size etc. as known in the art.

In the embodiment of FIG. 4, the first particle separator is similar to the item 03 of the fragmentation reactor. Embodiment 4 is also equipped with a secondary cyclone type particle separator (19). Both particle separators deliver particles to the bottom of item 11. In the lowermost position of item 11 a section (20) for stripping excess O2 from the fluidized particles are placed. Secondary fluidization and stripping gas inlets (22) for item 11 and 20 of the embodiment of FIG. 4 are distributed over the cross section using e.g spargers or other methods. Additional fluidization gas inlets may be present in item 11 on FIG. 4., but not shown. A stripping of product gas just before or after position (10) in FIG. 4 is also envisaged.

EXAMPLE

Example 1: Production of a Glycolaldehyde Rich $C_1$-$C_3$ Oxygenate Mixture by Thermolytic Fragmentation of a Sugar Solution The fragmentation of an aqueous solution of glucose was demonstrated in a riser type reactor unit. The particle inlet was placed upstream the feed inlet. The superficial gas velocity in the riser was approximately 6 m/s. The riser reactor length was 6.2 m with and inner diameter of 41 mm. Two cyclones followed the riser and the separated solids were admitted to an external reactor for reheating The residence time of the fragmentation product was approximately 1 second from feed inlet to first particle separator.

To collect the gaseous product, part of the gas stream exiting the second cyclone was directed to a condensation system The liquid product was rapidly condensed by indirect cooling at 1° C. and separated from the permanent gases. The flow of permanent gases was measured using a variable area flowmeter. The concentration of oxygenates in the liquid product was determined by HPLC analysis, and the yields calculated assuming that 8% of the mass of the feed was lost with the permanent gases due to incomplete condensation of water, i.e. using a mass balance of 92%. This is considered a conservative, but reasonable, assumption based on previous experience.

With this conservative assumption, about 60% of the carbon fed to the reactor was recovered as glycolaldehyde by thermolytic fragmentation of a 45 wt. % solution of glucose at approx. 500° C. Sodium silicate glass beads were used as bed material.

EMBODIMENTS

Embodiment 1. A process for thermolytic fragmentation of a sugar into $C_1$-$C_3$ oxygenates, said process comprising the steps of:
a. providing particles carrying heat and suitable for fluidization;
b. providing a fluidized bed fragmentation reactor comprising a riser and suitable for conducting thermolytic fragmentation and suitable for fluidizing a stream of particles;
c. providing a feedstock solution comprising a sugar;
d. introducing the particles into the reactor at a rate sufficient to maintain a temperature of at least 250° C., such as at least 300 350, 400 or 450° C., after the thermolytic fragmentation has taken place, and sufficient to obtain a fluidized stream of particles;
e. introducing the feedstock into the fluidized stream of particles to obtain thermolytic fragmentation of the sugar to produce a particle dense fragmentation product; then
f. separating a fraction of the particles from the particle dense fragmentation product to produce a particle lean fragmentation product;
g. quenching the particle lean fragmentation product at least 50° C. such that from introducing the feedstock into the particle containing fluidization stream to the quench is performed, the mean residence time of the gas is maximum 5, such as maximum 3 seconds, such as maximum 2, 1, 0.8 or 0.6 seconds;
h. recovering the crude fragmentation product,
i. transferring the particles separated in step f) to a reheater for heating; and
j. recirculating the heated particles to the fragmentation reactor.

Embodiment 2. The process according to embodiment 1, wherein the particle lean fragmentation product is subjected to a second particle separation step after step g) of quenching the particle lean fragmentation product and before step h) of recovering the crude fragmentation product.

Embodiment 3. The process according to any one of embodiments 1 or 2, wherein the reactor in the lower part comprises a particle inlet and a feedstock inlet, wherein the feedstock inlet is provided downstream the particle inlet.

Embodiment 4. The process according to embodiment 3, wherein the reactor in the lower part further comprises a fluidization stream inlet, and the fluidization inlet is provided upstream the particle inlet.

Embodiment 5. The process according to any one of embodiments 3 or 4, wherein the particles form a dense phase fluidized bed in the zone between the particle inlet and the feedstock inlet.

Embodiment 6. The process according to any one of embodiments 3-5, wherein the feedstock inlet is provided in the lower part of the riser.

Embodiment 7. The process according to any one of embodiments 1-5, wherein the reactor comprises a first particle separator downstream of the riser.

Embodiment 8. The process according to embodiment 7, wherein the reactor comprises a quench downstream the first particle separator.

Embodiment 9. The process according to embodiment 8, wherein the reactor comprises a second particle separator downstream the quench.

Embodiment 10. The process according to any one of embodiments 1-9, wherein the reactor does not comprise other means for heating than the heat carrying particles.

Embodiment 11. The process according to any one of embodiments 1-10, wherein the sugar is a mono- and/or di-saccharide.

Embodiment 12. The process according to any one of embodiments 1-11, wherein the feedstock solution comprises an aqueous solution of a sugar selected from the group consisting of sucrose, lactose, xylose, arabinose, ribose, mannose, tagatose, galactose, glucose and fructose; or mixtures thereof.

Embodiment 13. The process according to any one of embodiments 1-12, wherein the concentration of sugar in the feedstock solution is between 10 and 90% by weight.

Embodiment 14. The process according to any one of embodiments 1-13 wherein the temperature of the particles at the particle inlet of the fragmentation reactor is preferably at least 300° C., such as at least 400, 450, 500, 550, 600 or 650° C.

Embodiment 15. The process according to any one of embodiments 1-14 wherein the temperature of the particles at the particle inlet is within the range of from 300-800° C., such as in the range of from 400-800 or 450-650° C.

Embodiment 16. The process according to any one of embodiments 1-15 wherein the particles are selected from the group consisting of sand, silica, glass, alumina, steel, and silicon carbide.

Embodiment 17. The process according to any one of embodiments 1-16, wherein the mean particle size of the heat carrying particles is from 20-400 μm, such as from 20-300 20-200 or 20-100 μm.

Embodiment 18. The process according to any one of embodiments 1-17, wherein the particles of step a) are introduced into the fragmentation reactor at a mass flow rate of at least 10 kg/s.

Embodiment 19. The process according to any one of embodiments 1-18, wherein the velocity inside the fragmentation riser above the feedstock inlet is above 2 m/s, such as from 3-22, or from 5-20 m/s.

Embodiment 20. The process according to any one of embodiments 1-19, wherein the reheater comprises a fuel and combustion air inlet, a burner, a reheater particle inlet, a reheater riser, a reheater particle separator, a reheater gas outlet for flue gas and a reheater particle outlet.

Embodiment 21. The process according to any one of embodiments 1 to 20, wherein the temperature of the particles exiting the reheater particle outlet is in the range of from 300-800° C., such as in the range of from 400-800, 400-700 or 500-700° C.

Embodiment 22. The process according to any one of embodiments 20 or 21, wherein the burner is arranged within a burner chamber, which is separate from the reheater riser, and combustion gas from the burner chamber is led to the reheater riser.

Embodiment 23. The process according to any one of embodiments 20-22, wherein a part of the flue gas from the reheater after particulate removal is recirculated to the burner chamber.

Embodiment 24. The process according to any one of embodiments 1-23, wherein excess oxygen is stripped from the particles before they are transferred from the reheater to the fragmentation reactor.

Embodiment 25. A process for the preparation of a $C_1$-$C_3$ hydroxy compound from a sugar comprising the steps of:
carrying out a process according to any one of embodiments 1-24;
and then
subjecting the crude fragmentation product to a hydrogenation to obtain the corresponding $C_1$-$C_3$ hydroxy compound.

Embodiment 26. A system for fragmentation of a sugar composition into $C_1$-$C_3$ oxygenates comprising a fragmentation reactor, said reactor comprising within the reactor,
a riser
a first particle separator
a fluidization stream inlet
a particle inlet
a feedstock inlet
a particle outlet
a product outlet,
wherein the riser is arranged within and in the lower part of the fragmentation reactor; and the fluidization stream inlet and the particle inlet is arranged in the lower part of the riser; the feedstock inlet is arranged in the lower part of the riser; above the particle inlet the riser is adapted to fluidize particles in the riser; and the first particle separator is arranged in the upper part of the riser and is adapted to separate at least a part of the particles from a fluidization stream, and
wherein the fragmentation reactor further comprises a cooling section arranged downstream the first particle separator in relation to the gas stream, said cooling section being adapted to cool the fluidization stream exiting the first particle separator and the system further comprises a reheater for reheating particles exiting the fragmentation reactor, the reheater comprises a fuel and combustion air inlet, a burner, a reheater particle inlet, a reheater riser, a reheater particle separator, a reheater gas outlet and a reheater particle outlet.

Embodiment 27. The system according to embodiment 26, wherein the fragmentation reactor further comprises a second particle separator within the fragmentation reactor, said second particle separator being arranged in the upper part of the fragmentation reactor and being adapted to separate a further part of the particles from the fluidization stream.

Embodiment 28. The system according to any one of embodiments 26 or 27, wherein the cooling section is adapted to quench by injecting a liquid into the fragmentation reactor.

Embodiment 29. The system according to any one of embodiments 26 or 27, wherein the cooling section is adapted to quench by admitting a colder particle stream into the fragmentation reactor.

Embodiment 30. The system according to any one of embodiments 26 or 27, wherein the cooling section comprises an indirect heat exchanger.

Embodiment 31. The system according to any of embodiments 26-30, wherein the first particle separator is a low volume separator.

Embodiment 32. The system according to any of embodiments 26-31, wherein the first particle separator comprises at least one change of direction separator.

Embodiment 33. The system according to any of embodiments 26-32, wherein the first particle separator comprises at least one tube arranged with a first end at the upper part of and in fluid connection with the riser, and where the second end of the tube is pointing downwards and in fluid connection with the fragmentation reactor and outside the riser.

Embodiment 34. The system according to any of embodiments 27-33, wherein the second particle separator is at least one cyclone.

Embodiment 35. The system according to any of embodiments 26 to 34, wherein the burner and the reheater fuel and combustion air inlet is arranged upstream the reheater riser, and the reheater particle inlet is arranged in the lower part of the reheater riser downstream the burner, and the reheater particle inlet is in fluid connection with the fragmentation reactor particle outlet, the reheater riser being adapted to reheat the particles exiting the fragmentation reactor by means of combustion gas from the burner.

Embodiment 36. The system according to any of embodiments 26 to 35, wherein the reheater particle separator is arranged downstream the reheater riser, and the reheater particle outlet is in fluid connection with the fragmentation reactor particle inlet.

Embodiment 37. The system according to any of embodiments 26 to 36, wherein the burner is arranged in a separate burner chamber.

Embodiment 38. The system according to embodiment 37, wherein the burner chamber is separated from the riser by a constriction.

Embodiment 39. The system according to any of embodiments 26 to 38, wherein a stripping chamber is arranged downstream the reheater particle separator and upstream the fragmentation reactor particle inlet.

The invention claimed is:

1. A process for thermolytic fragmentation of a sugar into $C_1$-$C_3$ oxygenates, said process comprising the steps of:
   a. providing particles carrying heat and suitable for fluidization;
   b. providing a fluidized bed fragmentation reactor comprising a riser and suitable for conducting thermolytic fragmentation and suitable for fluidizing a stream of particles;
   c. providing a feedstock solution comprising a sugar;
   d. introducing the particles into the reactor at a rate sufficient to maintain a temperature of at least 250° C. after the thermolytic fragmentation has taken place, and sufficient to obtain a fluidized stream of particles;
   e. introducing the feedstock into the fluidized stream of particles to obtain thermolytic fragmentation of the sugar to produce a particle dense fragmentation product; then
   f. separating a fraction of the particles from the particle dense fragmentation product to produce a particle lean fragmentation product in a first particle separator, wherein the first particle separator is a riser terminator arranged immediately after the riser and is adapted to separate at least a part of the particles from the particle dense fragmentation product;
   g. quenching the particle lean fragmentation product at least 50° C. such that from introducing the feedstock into the particle containing fluidization stream to the quench is performed, the mean residence time of the gas is maximum 5 seconds;

h. recovering the crude fragmentation product,
i. transferring the particles separated in step f) to a reheater for heating; and
j. recirculating the heated particles to the fragmentation reactor.

2. The process according to claim 1, wherein the feedstock inlet is provided in the lower part of the riser.

3. The process according to claim 1, wherein the reactor comprises a quench downstream the first particle separator.

4. The process according to claim 1, wherein the sugar is a mono-and/or di-saccharide.

5. The process according to claim 1, wherein the feedstock solution comprises an aqueous solution of a sugar selected from the group consisting of sucrose, lactose, xylose, arabinose, ribose, mannose, tagatose, galactose, glucose, fructose, and mixtures thereof.

6. The process according to claim 1, wherein the concentration of sugar in the feedstock solution is between 10 and 90% by weight.

7. The process according to claim 1, wherein the temperature of the particles at the particle inlet of the fragmentation reactor is at least 300° C.

8. The process according to claim 1, wherein the reheater comprises a fuel and combustion air inlet, a burner, a reheater particle inlet, a reheater riser, a reheater particle separator, a reheater gas outlet for flue gas and a reheater particle outlet.

9. The process according to claim 8, wherein the temperature of the particles exiting the reheater particle outlet is in the range of from 300-800° C.

10. The process according to claim 8, wherein the burner is arranged within a burner chamber, which is separate from the reheater riser, and combustion gas from the burner chamber is led to the reheater riser.

11. The process according to claim 1, wherein excess oxygen is stripped from the particles before they are transferred from the reheater to the fragmentation reactor.

12. A process for the preparation of a $C_1$-$C_3$ hydroxy compound from a sugar comprising the steps of:
carrying out a process according to claim 1;
and then
subjecting the crude fragmentation product to a hydrogenation to obtain the corresponding $C_1$-$C_3$ hydroxy compound.

13. A system for fragmentation of a sugar composition into $C_1$-$C_3$ oxygenates comprising a fragmentation reactor, said reactor comprising within the reactor,
a riser
a first particle separator
a fluidization stream inlet
a particle inlet
a feedstock inlet
a particle outlet
a product outlet,
wherein the riser is arranged within and in the lower part of the fragmentation reactor; and the fluidization stream inlet and the particle inlet is arranged in the lower part of the riser; the feedstock inlet is arranged in the lower part of the riser above the particle inlet; the riser is adapted to fluidize particles in the riser; and the first particle separator is arranged in the upper part of the riser and is adapted to separate at least a part of the particles from a fluidization stream, and
wherein the fragmentation reactor further comprises a cooling section arranged downstream the first particle separator in relation to the gas stream, said cooling section being adapted to cool the fluidization stream exiting the first particle separator and the system further comprises a reheater for reheating particles exiting the fragmentation reactor, the reheater comprises a fuel and combustion air inlet, a burner, a reheater particle inlet, a reheater riser, a reheater particle separator, a reheater gas outlet and a reheater particle outlet.

14. The system according to claim 13, wherein the cooling section is adapted to quench by injecting a liquid into the fragmentation reactor.

15. The system according to claim 13, wherein the first particle separator is a low volume separator.

16. The system according to claim 13, wherein the first particle separator comprises at least one change of direction separator.

17. The system according to claim 13, wherein the burner and the reheater fuel and combustion air inlet is arranged upstream the reheater riser, and the reheater particle inlet is arranged in the lower part of the reheater riser downstream the burner, and the reheater particle inlet is in fluid connection with the fragmentation reactor particle outlet, the reheater riser being adapted to reheat the particles exiting the fragmentation reactor by means of combustion gas from the burner.

18. The system according to claim 13, wherein the reheater particle separator is arranged downstream the reheater riser, and the reheater particle outlet is in fluid connection with the fragmentation reactor particle inlet.

19. The system according to claim 13, wherein the burner is arranged in a separate burner chamber.

20. The system according to claim 19, wherein the burner chamber is separated from the riser by a constriction.

21. The system according to claim 13, wherein a stripping chamber is arranged downstream the reheater particle separator and upstream the fragmentation reactor particle inlet.

22. The process according to claim 1, wherein the first particle separator comprises at least one tube arranged with a first end at the upper part of and in fluid connection with the riser, and where the second end of the tube is arranged to change a direction of flow of particles by 90 to 180 degrees and is in fluid connection with and within the fragmentation reactor and outside the riser.

23. A process for thermolytic fragmentation of a sugar into $C_1$-$C_3$ oxygenates, said process comprising the steps of:
a. providing particles carrying heat and suitable for fluidization;
b. providing a fluidized bed fragmentation reactor comprising a riser and suitable for conducting thermolytic fragmentation and suitable for fluidizing a stream of particles;
c. providing a feedstock solution comprising a sugar;
d. introducing the particles into the reactor at a rate sufficient to maintain a temperature of at least 250° C. after the thermolytic fragmentation has taken place, and sufficient to obtain a fluidized stream of particles;
e. introducing the feedstock into the fluidized stream of particles to obtain thermolytic fragmentation of the sugar to produce a particle dense fragmentation product; then
f. separating a fraction of the particles from the particle dense fragmentation product to produce a particle lean fragmentation product in a first particle separator, wherein the first particle separator is arranged in an upper part of the riser and is adapted to separate at least a part of the particles from the particle dense fragmentation product;
g. quenching the particle lean fragmentation product at least 50° C. such that from introducing the feedstock into the particle containing fluidization stream to the quench is performed, the mean residence time of the gas is maximum 5 seconds;

h. recovering the crude fragmentation product, i. transferring the particles separated in step f) to a reheater for heating; and j. recirculating the heated particles to the fragmentation reactor.

24. The process according to claim 23, wherein the feedstock inlet is provided in the lower part of the riser.

25. The process according to claim 23, wherein the reactor comprises a quench downstream the first particle separator.

26. The process according to claim 23, wherein the sugar is a mono- and/or di-saccharide.

27. The process according to claim 23, wherein the feedstock solution comprises an aqueous solution of a sugar selected from the group consisting of sucrose, lactose, xylose, arabinose, ribose, mannose, tagatose, galactose, glucose, fructose, and mixtures thereof.

28. The process according to claim 23, wherein the concentration of sugar in the feedstock solution is between 10 and 90% by weight.

29. The process according to claim 23, wherein the temperature of the particles at the particle inlet of the fragmentation reactor is at least 300° C.

30. The process according to claim 23, wherein the reheater comprises a fuel and combustion air inlet, a burner, a reheater particle inlet, a reheater riser, a reheater particle separator, a reheater gas outlet for flue gas and a reheater particle outlet.

31. The process according to claim 30, wherein the temperature of the particles exiting the reheater particle outlet is in the range of from 300-800° C.

32. The process according to claim 30, wherein the burner is arranged within a burner chamber, which is separate from the reheater riser, and combustion gas from the burner chamber is led to the reheater riser.

33. The process according to claim 23, wherein excess oxygen is stripped from the particles before they are transferred from the reheater to the fragmentation reactor.

34. A process for the preparation of a $C_1$-$C_3$ hydroxy compound from a sugar comprising the steps of:
carrying out a process according to claim 23;
and then
subjecting the crude fragmentation product to a hydrogenation to obtain the corresponding $C_1$-$C_3$ hydroxy compound.

35. A process for thermolytic fragmentation of a sugar into $C_1$-$C_3$ oxygenates, said process comprising the steps of:
a. providing particles carrying heat and suitable for fluidization;
b. providing a fluidized bed fragmentation reactor comprising a riser and suitable for conducting thermolytic fragmentation and suitable for fluidizing a stream of particles;
c. providing a feedstock solution comprising a sugar;
d. introducing the particles into the reactor at a rate sufficient to maintain a temperature of at least 250° C. after the thermolytic fragmentation has taken place, and sufficient to obtain a fluidized stream of particles;
e. introducing the feedstock into the fluidized stream of particles to obtain thermolytic fragmentation of the sugar to produce a particle dense fragmentation product; then
f. separating a fraction of the particles from the particle dense fragmentation product to produce a particle lean fragmentation product in a first particle separator, wherein the first particle separator is adapted to separate at least 50% by weight of the particles from the particle dense fragmentation product;
g. quenching the particle lean fragmentation product at least 50° C. such that from introducing the feedstock into the particle containing fluidization stream to the quench is performed, the mean residence time of the gas is maximum 5 seconds;
h. recovering the crude fragmentation product,
i. transferring the particles separated in step f) to a reheater for heating; and
j. recirculating the heated particles to the fragmentation reactor.

36. The process according to claim 35, wherein the first particle separator is a change of direction separator.

37. A process for the preparation of a $C_1$-$C_3$ hydroxy compound from a sugar comprising the steps of:
carrying out a process according to claim 35;
and then
subjecting the crude fragmentation product to a hydrogenation to obtain the corresponding $C_1$-$C_3$ hydroxy compound.

38. A process for thermolytic fragmentation of a sugar into $C_1$-$C_3$ oxygenates, said process comprising the steps of:
a. providing particles carrying heat and suitable for fluidization;
b. providing a fluidized bed fragmentation reactor comprising a riser and suitable for conducting thermolytic fragmentation and suitable for fluidizing a stream of particles;
c. providing a feedstock solution comprising a sugar;
d. introducing the particles into the reactor at a rate sufficient to maintain a temperature of at least 250° C. after the thermolytic fragmentation has taken place, and sufficient to obtain a fluidized stream of particles;
e. introducing the feedstock into the fluidized stream of particles to obtain thermolytic fragmentation of the sugar to produce a particle dense fragmentation product; then
f. separating a fraction of the particles from the particle dense fragmentation product to produce a particle lean fragmentation product;
g. quenching the particle lean fragmentation product at least 50° C. such that from introducing the feedstock into the particle containing fluidization stream to the quench is performed, the mean residence time of the gas is maximum 5 seconds;
h. recovering the crude fragmentation product,
i. transferring the particles separated in step f) to a reheater for heating, wherein the reheater comprises a fuel and combustion air inlet, a burner, a reheater particle inlet, a reheater riser, a reheater particle separator, a reheater gas outlet for flue gas and a reheater particle outlet; and
j. recirculating the heated particles to the fragmentation reactor.

39. A process for the preparation of a $C_1$-$C_3$ hydroxy compound from a sugar comprising the steps of:
carrying out a process according to claim 38;
and then
subjecting the crude fragmentation product to a hydrogenation to obtain the corresponding $C_1$-$C_3$ hydroxy compound.

* * * * *